(12) United States Patent
Randolph et al.

(10) Patent No.: US 8,034,095 B2
(45) Date of Patent: Oct. 11, 2011

(54) INTRALUMINAL SYSTEM FOR RETRIEVING AN IMPLANTABLE MEDICAL DEVICE

(75) Inventors: James R. Randolph, Bloomington, IN (US); Sean D. Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 429 days.

(21) Appl. No.: 12/201,556

(22) Filed: Aug. 29, 2008

(65) Prior Publication Data
US 2010/0057184 A1  Mar. 4, 2010

(51) Int. Cl.
*A61F 2/06* (2006.01)
(52) U.S. Cl. .................................... 623/1.12
(58) Field of Classification Search .............. 606/108, 606/129, 200; 623/1.11
See application file for complete search history.

(56) References Cited

U.S. PATENT DOCUMENTS

| | | | |
|---|---|---|---|
| 4,611,594 A | 9/1986 | Grayhack et al. | |
| 4,990,151 A | 2/1991 | Wallstén | |
| 5,843,028 A * | 12/1998 | Weaver et al. | 604/514 |
| 5,968,053 A | 10/1999 | Revelas | |
| 6,027,509 A | 2/2000 | Schatz et al. | |
| 6,241,738 B1 | 6/2001 | Dereume | |
| 6,350,271 B1 | 2/2002 | Kurz et al. | |
| 6,652,569 B1 * | 11/2003 | Taylor et al. | 623/1.11 |
| 6,676,692 B2 * | 1/2004 | Rabkin et al. | 623/1.11 |
| 6,800,080 B1 * | 10/2004 | Bates | 606/127 |
| 7,029,488 B2 | 4/2006 | Schönholz et al. | |
| 7,101,380 B2 * | 9/2006 | Khachin et al. | 606/127 |
| 7,291,154 B2 | 11/2007 | Maitland et al. | |
| 7,553,314 B2 * | 6/2009 | Khachin et al. | 606/127 |
| 7,611,525 B2 * | 11/2009 | Baig | 606/194 |
| 7,713,275 B2 * | 5/2010 | Greenberg et al. | 606/108 |
| 7,753,917 B2 * | 7/2010 | Urbanski et al. | 606/108 |
| 7,753,918 B2 * | 7/2010 | Hartley et al. | 606/108 |
| 7,776,052 B2 * | 8/2010 | Greenberg et al. | 606/108 |
| 2002/0169474 A1 * | 11/2002 | Kusleika et al. | 606/200 |
| 2004/0181237 A1 | 9/2004 | Forde et al. | |
| 2005/0059993 A1 | 3/2005 | Ramzipoor et al. | |
| 2005/0187570 A1 | 8/2005 | Nguyen et al. | |
| 2006/0282113 A1 | 12/2006 | Sater | |
| 2007/0027520 A1 | 2/2007 | Sherburne | |

* cited by examiner

*Primary Examiner* — Gary Jackson
*Assistant Examiner* — Amy Shipley
(74) *Attorney, Agent, or Firm* — Brinks Hofer Gilson & Lione

(57) ABSTRACT

An intraluminal system for retrieving an implantable medical device from a body vessel includes, according to one embodiment, a grasping component including at least one deployable arm, where a proximal end of the arm is configured to extend away from a longitudinal axis of the system when deployed, and a first sheath disposed adjacent to the grasping component, where the first sheath includes a radially expandable portion at a distal end thereof. A second sheath overlies the first sheath and the grasping component. Relative motion between the second sheath and the grasping component allows the proximal end of the deployable arm to be deployed for grasping a distal portion of an implantable medical device, and relative motion between the second sheath and the first sheath allows the expandable portion of the first sheath to radially expand to receive a proximal portion of the implantable medical device.

9 Claims, 15 Drawing Sheets

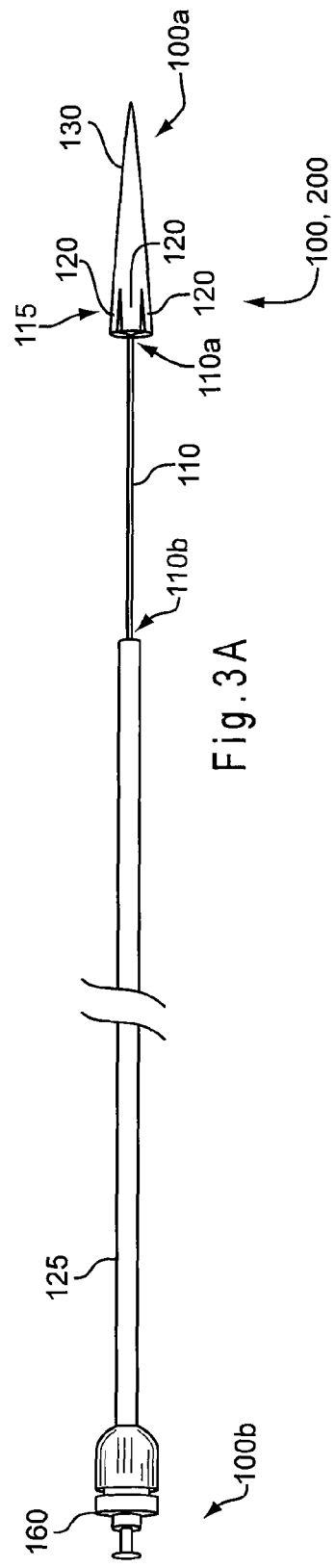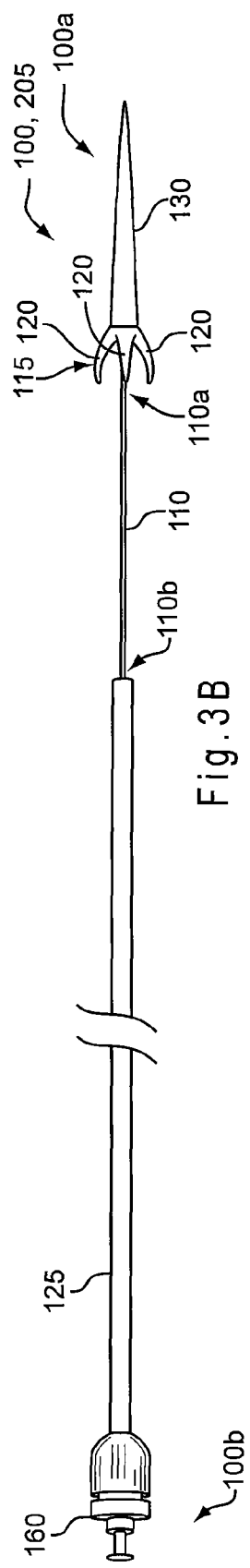

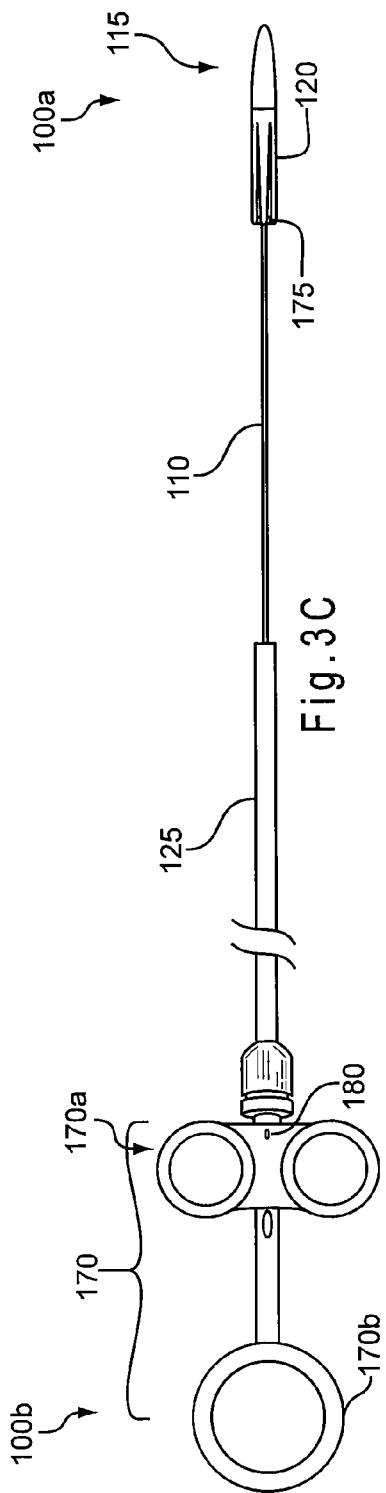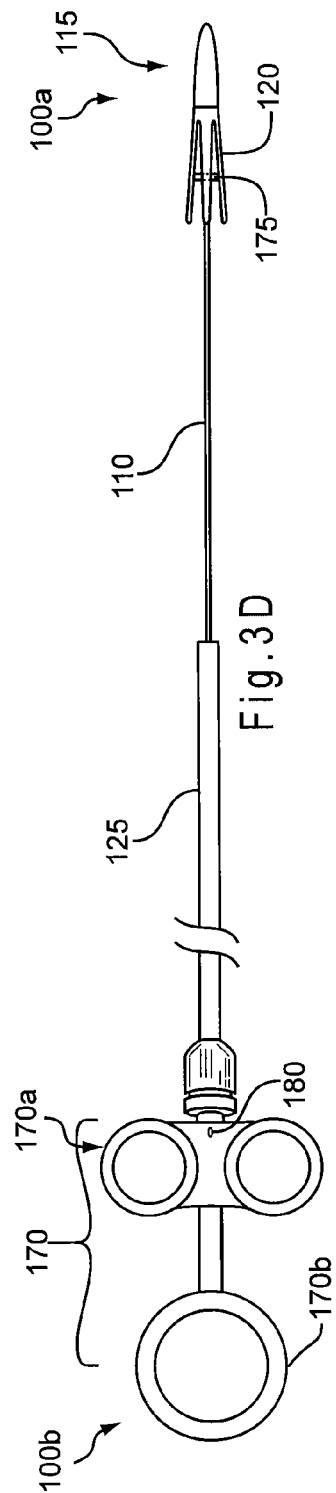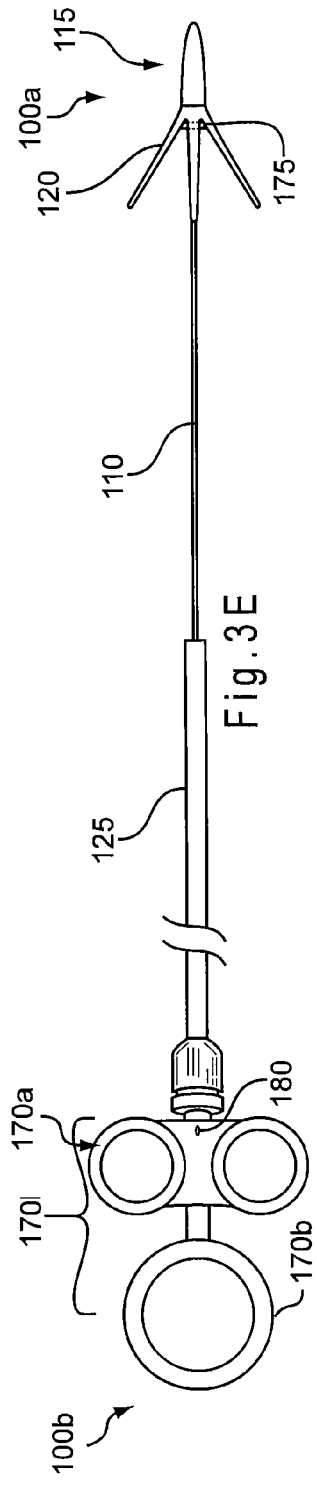

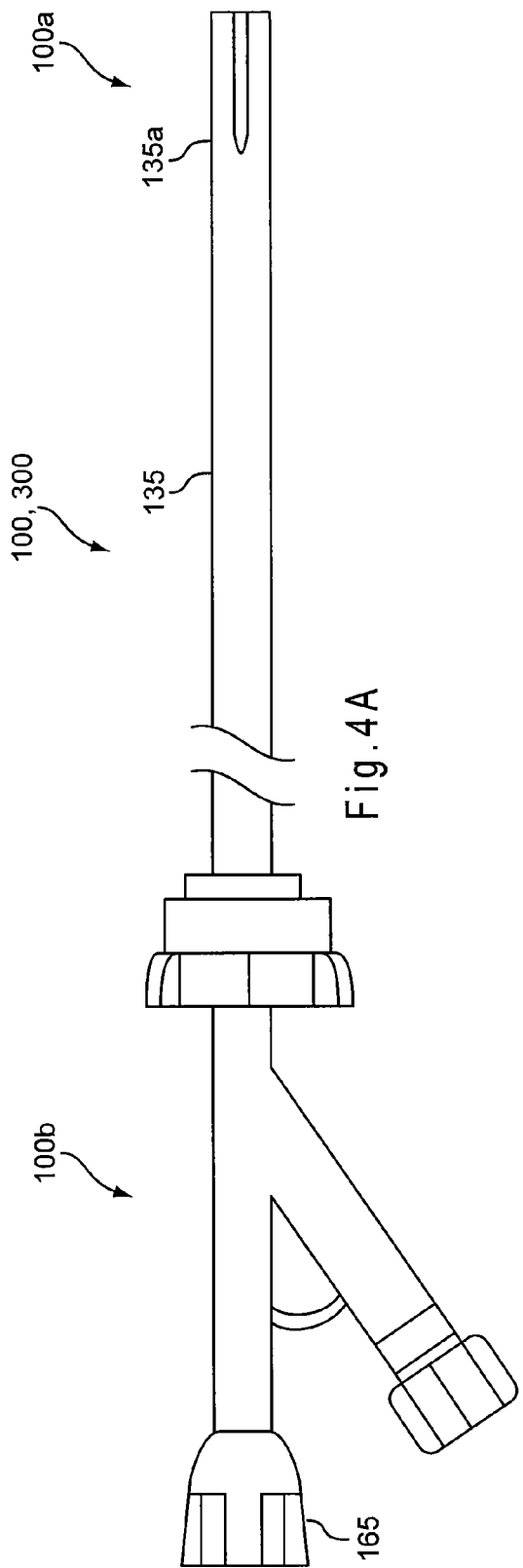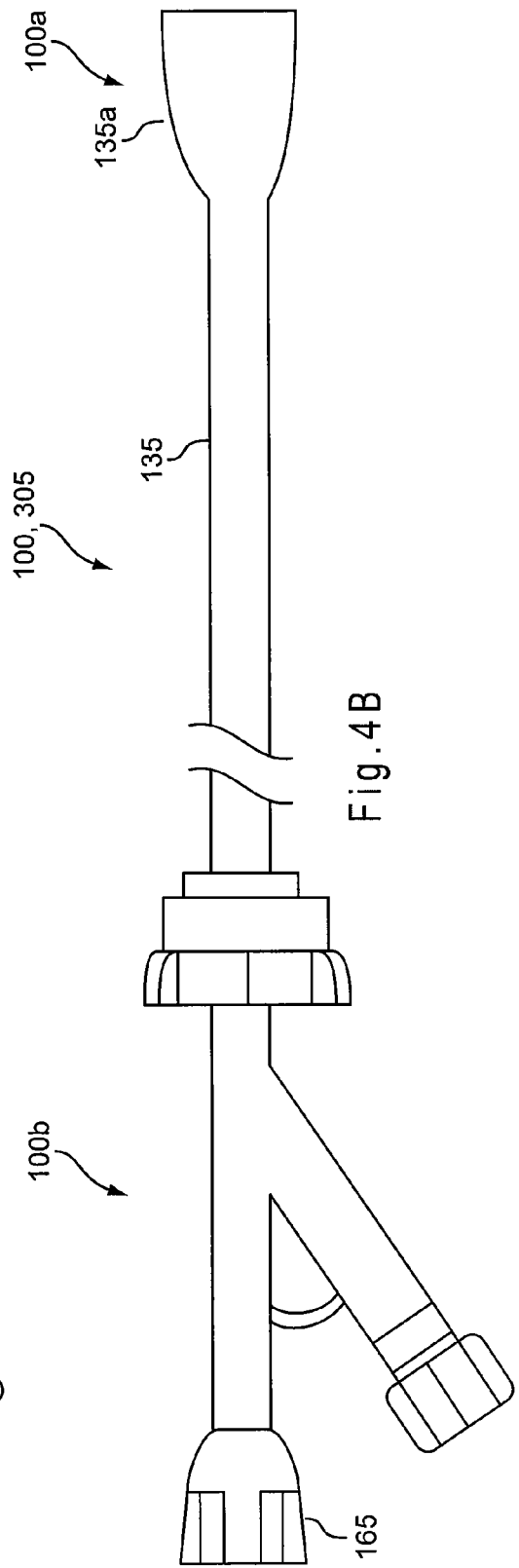

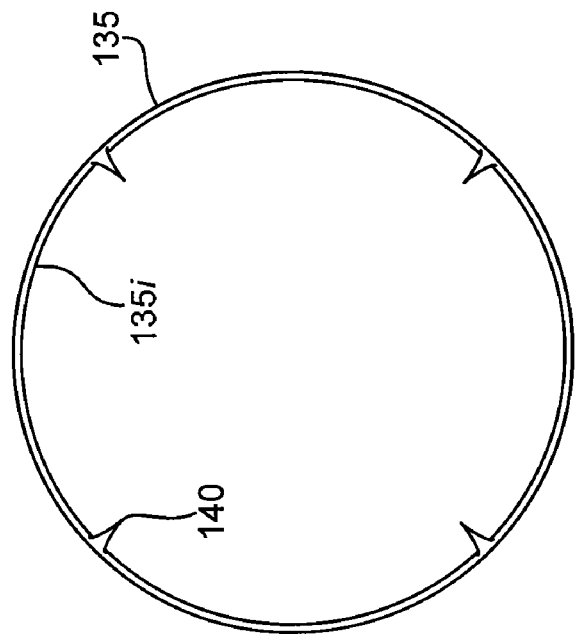
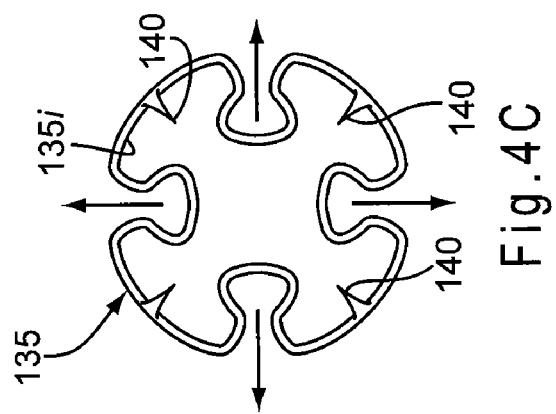
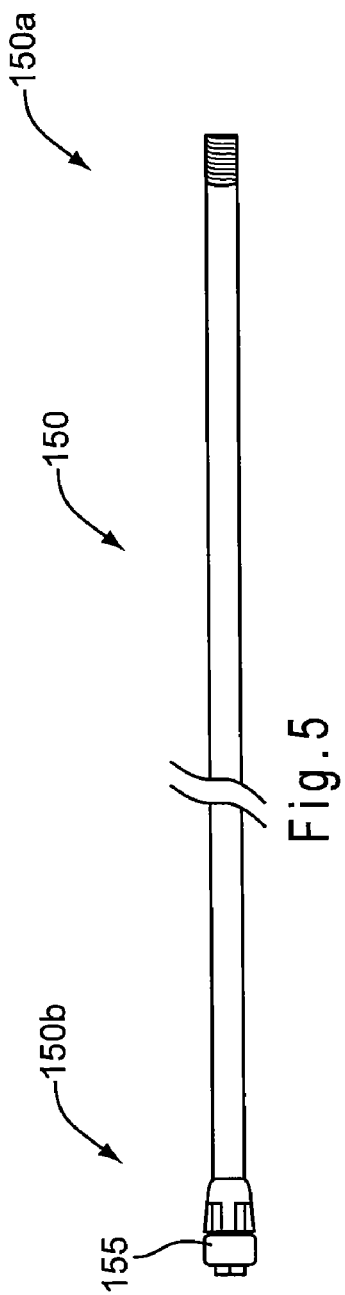
Fig. 4D
Fig. 4C
Fig. 5

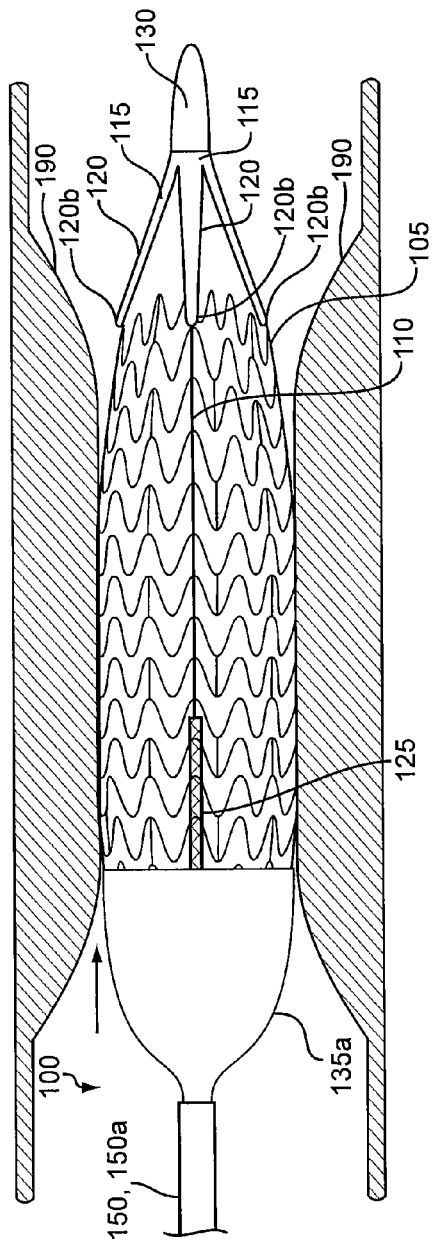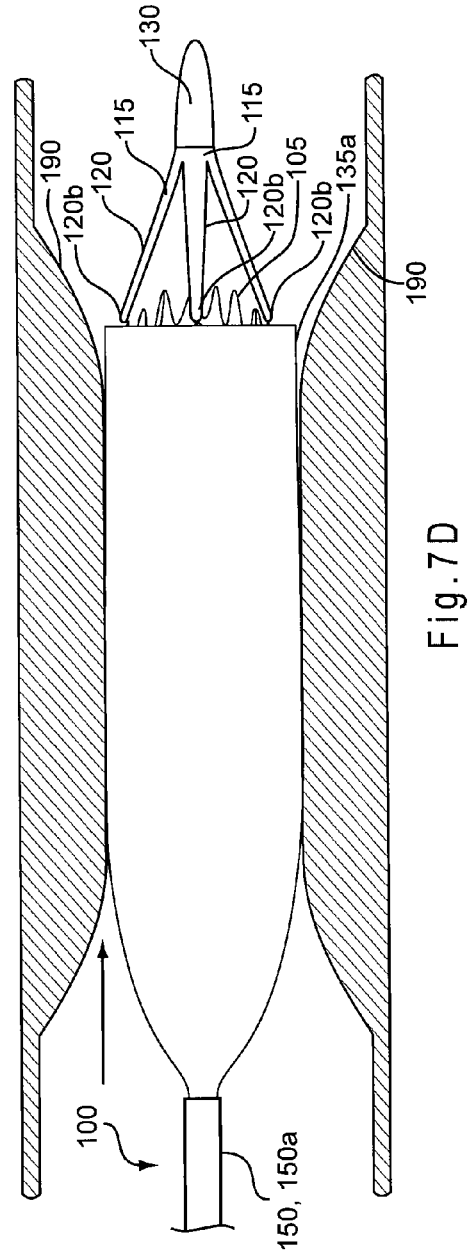

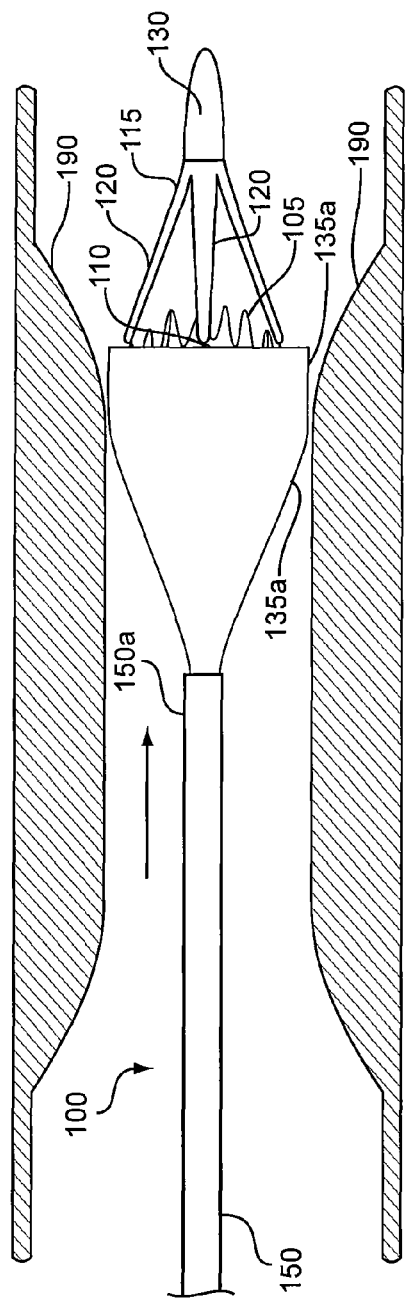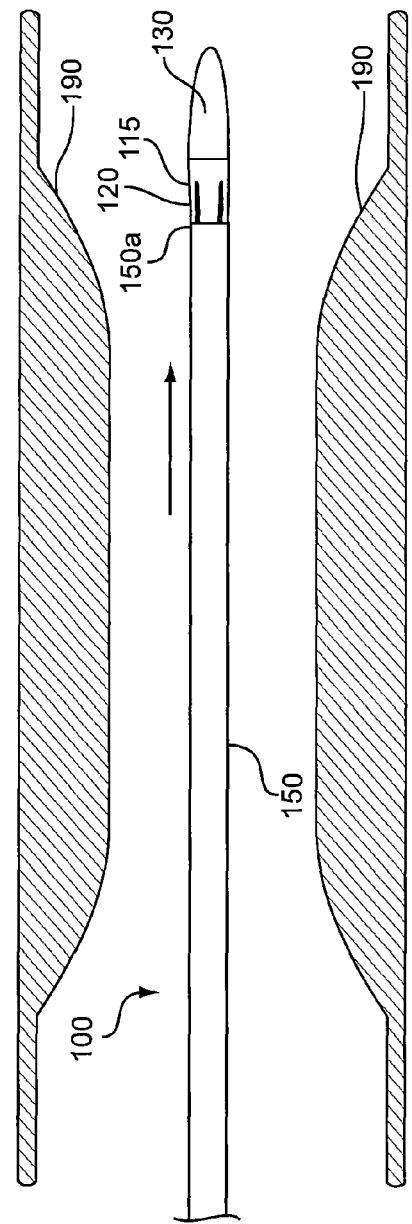
Fig. 7E
Fig. 7F

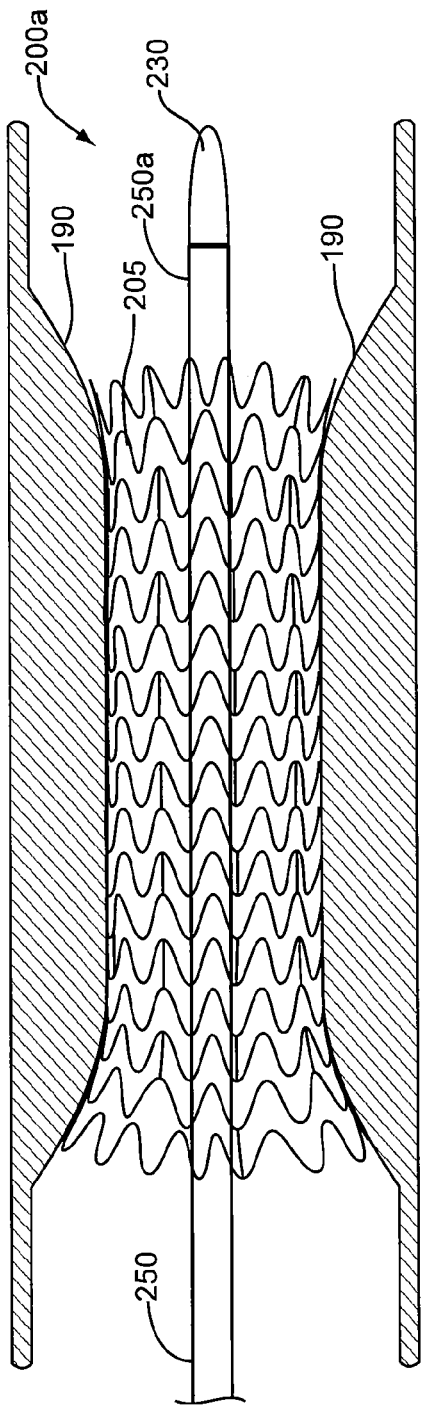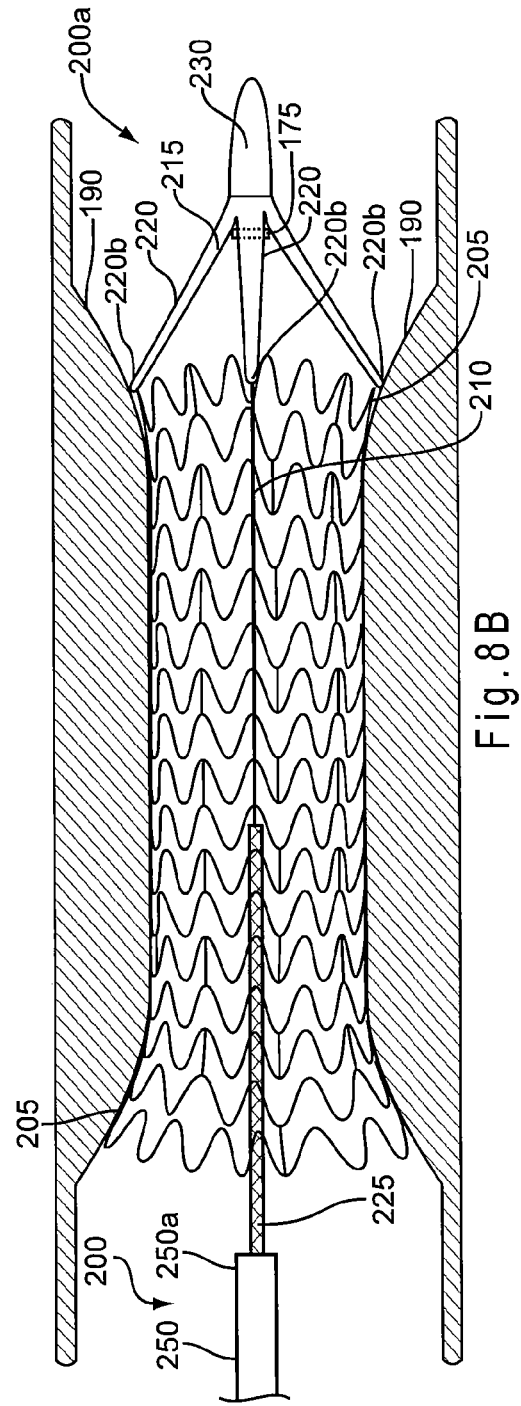
Fig. 8A
Fig. 8B

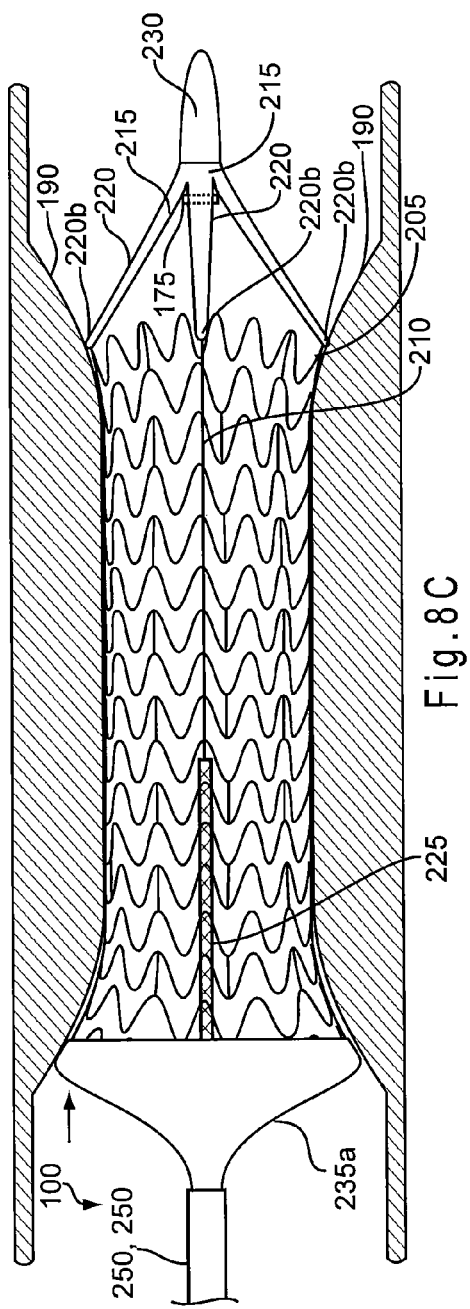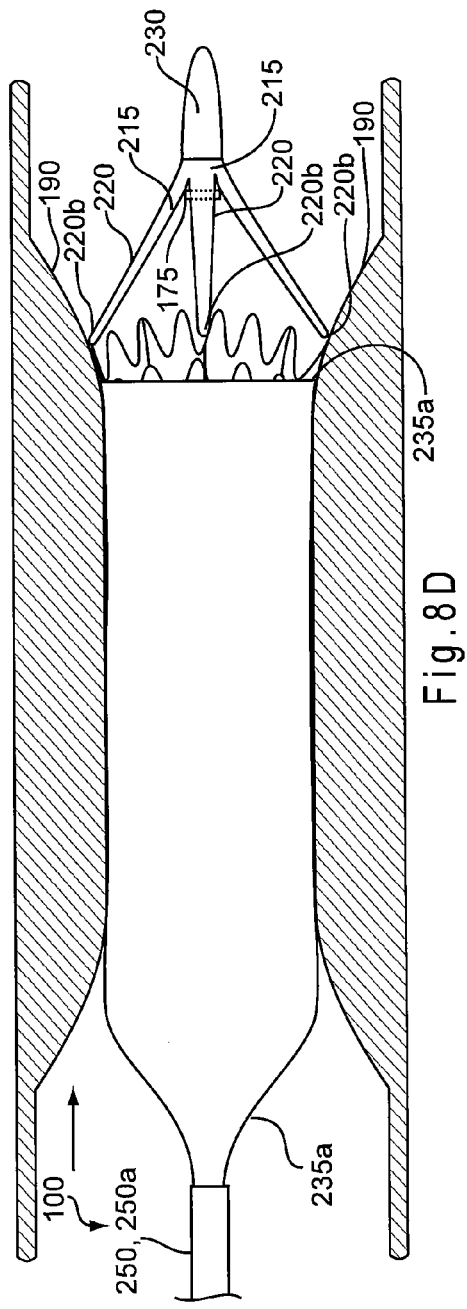

INTRALUMINAL SYSTEM FOR RETRIEVING AN IMPLANTABLE MEDICAL DEVICE

TECHNICAL FIELD

The present disclosure is generally related to medical devices, and more particularly to intraluminal systems for retrieving implantable medical devices from body vessels.

BACKGROUND

Stents are tubular support structures that may be implanted into body vessels to treat blockages, occlusions, narrowing ailments and other problems that may restrict flow through the vessel. Numerous vessels throughout the vascular system, including peripheral arteries, such as the carotid, brachial, renal, iliac and femoral arteries, and other vessels, may benefit from treatment by a stent. Generally, a stent comprises a framework of interconnected struts that allows the stent to be collapsed into a low profile configuration for delivery into the vessel and then radially expanded at the treatment site to support the vessel wall. Balloon-expandable stents expand in response to the inflation of a balloon, whereas self-expanding stents deploy automatically when released from a delivery device.

In some instances it may be necessary to remove a stent or other medical device that has been implanted in a vessel. The stent may have been deployed improperly (e.g., not fully expanded), for example, or positioned at an undesirable location in the vessel. To safely and successfully retrieve a device under these circumstances, open surgery is usually needed.

BRIEF SUMMARY

An intraluminal system that can safely and effectively retrieve an implanted medical device from a body vessel without open surgery is described herein. A method of retrieving an implanted medical device from a body vessel is also described. The intraluminal system and method are designed to allow the implanted device to be collapsed to a low-profile configuration and retrieved from the vessel without causing damage to the surrounding tissue.

The system includes, according to one embodiment, a grasping component including at least one deployable arm, where a proximal end of the arm is configured to extend away from a longitudinal axis of the system when deployed, and a first sheath disposed adjacent to the grasping component, where the first sheath includes a radially expandable portion at a distal end thereof. A second sheath overlies the first sheath and the grasping component. Relative motion between the second sheath and the grasping component allows the proximal end of the deployable arm to be deployed for grasping a distal portion of an implantable medical device, and relative motion between the second sheath and the first sheath allows the expandable portion of the first sheath to radially expand to receive a proximal portion of the implantable medical device.

The system includes, according to a second embodiment, a grasping component, and a first sheath disposed adjacent to the grasping component, where the first sheath includes a radially expandable portion at a distal end thereof and comprises an arrangement of barbs on an inner wall of the expandable portion. A second sheath overlies the first sheath and the grasping component. Relative motion between the second sheath and the grasping component allows the grasping component to be deployed for grasping a distal portion of an implantable medical device, and relative motion between the second sheath and the first sheath allows the expandable portion of the first sheath to radially expand to receive a proximal portion of the implantable medical device.

The method comprises positioning a retrieval system adjacent to a medical device to be removed from a body vessel, where the retrieval system includes a grasping component, a first sheath having a radially expandable portion disposed adjacent to the grasping component, and a second sheath overlying the first sheath and the grasping component. The grasping component is deployed to contact a distal portion of the medical device. The expandable portion of the first sheath is expanded and advanced over a proximal portion of the medical device. A second sheath is advanced over the expandable portion of the first sheath to collapse the expandable portion and the medical device to a low profile configuration. The grasping component is also collapsed to a low profile configuration. The system, including the medical device, is then removed from the body vessel.

BRIEF DESCRIPTION OF THE DRAWINGS

FIG. 1A shows a close-up view of a component of the system of FIG. 1;

FIG. 3A shows selected components of the system, including one embodiment of a grasping component in a low-profile or delivery configuration;

FIG. 3B shows selected components of the system, including the grasping component of FIG. 3A in a deployed configuration;

FIG. 3C shows selected components of the system, including another embodiment of the grasping component in a low-profile or delivery configuration;

FIG. 3D shows selected components of the system, including the grasping component of FIG. 3C in a partially deployed configuration;

FIG. 3E shows selected components of the system, including the grasping component of FIG. 3C in a fully deployed configuration;

FIG. 4A shows selected components of the system, including an expandable portion of a first sheath in a low-profile or delivery configuration;

FIG. 4B shows selected components of the system, including the expandable portion of the first sheath in a deployed configuration;

FIG. 4C shows a transverse cross-sectional view of the expandable portion of the first sheath shown in FIG. 4A;

FIG. 4D shows a transverse cross-sectional view of the expandable portion of the first sheath shown in FIG. 4B;

FIG. 5 shows selected components of the system, including the second sheath;

FIGS. 7A-7G show steps of an exemplary method of retrieving an implantable medical device that has failed to deploy properly or is undersized with respect to the vessel diameter; and FIGS. 8A-8G show steps of an exemplary method of retrieving an implantable medical device that has been placed at an improper location in the vessel.

DETAILED DESCRIPTION OF THE DRAWINGS AND THE PRESENTLY PREFERRED EMBODIMENTS

Figure 1:
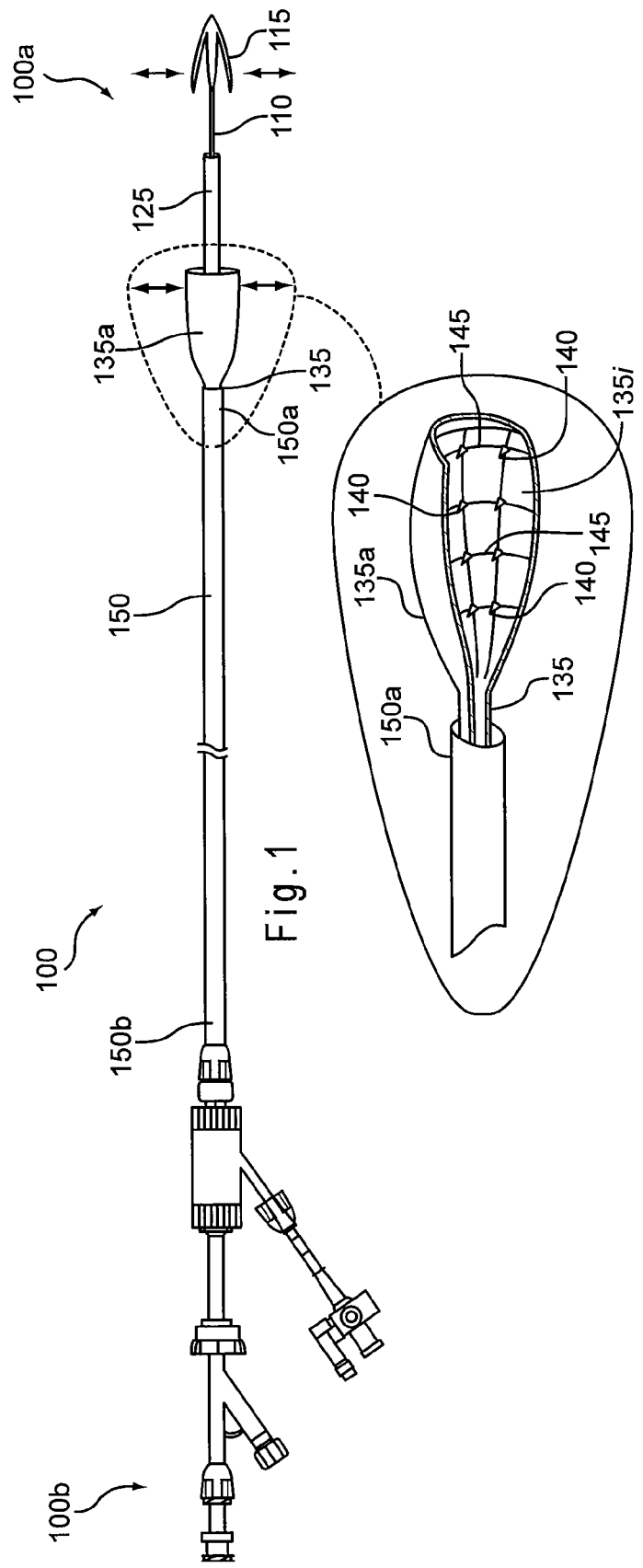
FIG. 1 shows, according to one embodiment, a system for retrieving an implantable medical device from a body vessel.
Figure 2:
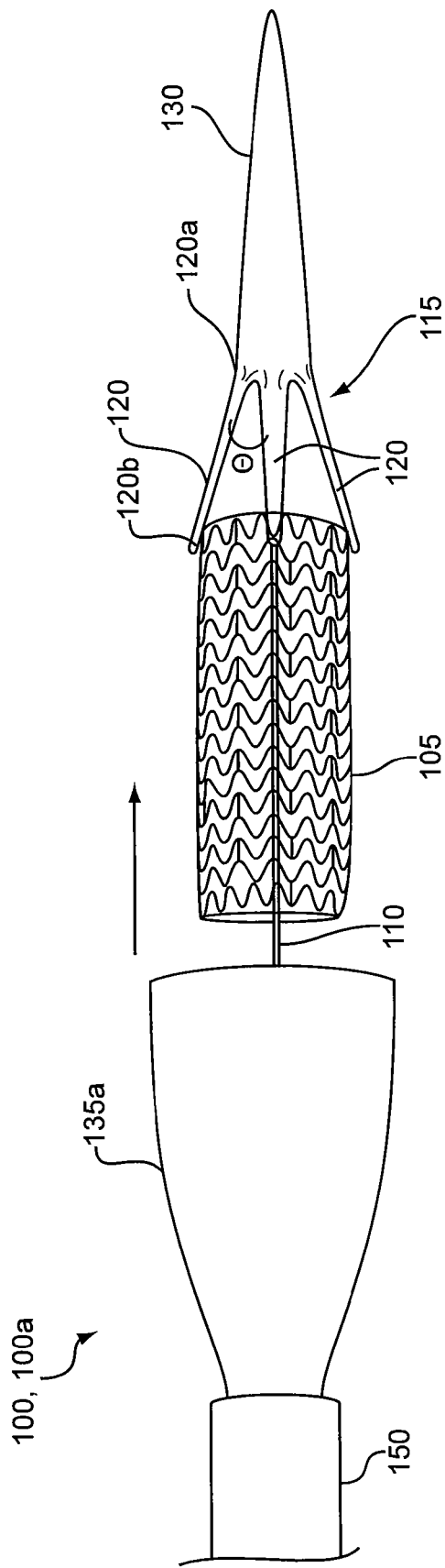
FIG. 2 shows a close-up view of a distal end of the system of FIG. 1.

FIGS. 1 and 2 show, according to one embodiment, a system 100 for retrieving an implantable medical device from a body vessel. In FIG. 1 the distal end 100a and the proximal end 100b of the system 100 are depicted with the distal end 100a shown in a deployed configuration. FIG. 2 provides a close-up view of the distal end 100a of the system 100 being used to retrieve a stent 105.

Among the basic elements of the retrieval system 100 are a grasping component 115 used to grasp a distal portion of the medical device to be retrieved from the body vessel, and a first sheath 135 including an expandable portion 135a that is advanced over the medical device as it is held in place by the grasping component 115. As shown in FIG. 1A, the expandable portion 135a of the first sheath 135 includes an arrangement of barbs 140 configured to ratchet over structural elements of the medical device (e.g., struts of a stent) as it is advanced, thereby anchoring the medical device to the first sheath 135. After the first sheath 135 is advanced and the medical device is "captured," a second sheath 150 is pushed distally over the first sheath 135 to collapse the sheath 135 and the medical device to a low-profile configuration. The grasping component 115 is also collapsed, preferably by the first sheath 135. The retrieval system 100, including the captured medical device, can thus be removed from the body without causing damage to the vessel.

In FIGS. 3A-3E, 4A-4D, and 5, various components of the retrieval system 100 are shown separately from the system as a whole.

FIGS. 3A and 3B show the innermost components of the system 100 in a low-profile configuration 200 and a deployed configuration 205, respectively. The system 100 includes an inner tubular member or cannula 110 and a grasping component 115 including at least one deployable arm 120. The grasping component 115 is attached to the cannula 110 at a distal end 110a thereof. The cannula 110 includes a lumen sized to accommodate a guide wire and has a wall thickness sufficient to provide adequate pushability. A push rod 125 extending to a luer 160 at the proximal end 100b of the system 100 is attached to a proximal portion of the cannula 110. The cannula 110 may be integrally formed with the push rod 125 or have a shorter length with a proximal portion 110b glued, embedded into, or otherwise attached to a distal end of the push rod 125, as shown in FIGS. 3A and 3B. Alternatively the cannula 110 may pass through a lumen of the push rod 125 such that the proximal portion reaches the luer 160. The cannula 110 has a smaller diameter than the push rod 125 so as to provide room for the expandable portion 135a of the first sheath 135 to collapse or fold up during delivery of the system 100 and also to serve as a chamber for carrying the collapsed and captured stent.

Preferably, the system 100 includes at least two deployable arms 120. The exemplary system 100 shown in FIGS. 3A and 3B includes four deployable arms 120. It may be advantageous for the deployable arms 120 to be symmetrically positioned about a circumference of the grasping component 115. Referring again to FIG. 2, each deployable arm 120 has a distal end 120a and a proximal end 120b. In the low-profile configuration, the deployable arms are disposed adjacent to the cannula 110. When deployed, the proximal end 120b of each deployable arm 120 swings or otherwise extends away from the cannula 110 toward the body vessel. The arms 120 may automatically extend or be manually extended. The deployable arms 120 open in the direction of the proximal end 100b of the system 100 and preferably form an acute angle θ with respect to a longitudinal axis of the system (e.g, as defined by the cannula 110). The grasping component 115 may be attached to or may form an integral part of a distal tip 130 of the system 100. The deployable arms 120 may be collapsed from the extended position by advancing the first sheath 135 and/or the second sheath 150 over the arms 120, as will be discussed further below.

Alternatively, as shown in FIGS. 3C through 3E, the grasping component 115 may include an umbrella mechanism to manually collapse and/or extend the deployable arms 120. The umbrella mechanism may take the form of an annular fixture 175 slidingly disposed about the cannula 110 and in communication with the arms 120 and the controller 170. By translating the proximal portion 170b of the controller 170 with respect to the distal portion 170a of the controller 170, the umbrella mechanism 175 may be advanced (or retracted) to extend (or collapse) the deployable arms 120. As shown in the figures, the controller 170 may include a guide wire port 180.

FIGS. 4A-4D show another portion of the system 100 in a low-profile configuration 300 (FIGS. 4A and 4C) and a deployed configuration 305 (FIGS. 4B and 4D). The system 100 includes a tubular first sheath 135 having an expandable portion 135a that overlies the cannula 110, as can be seen in FIG. 2. The expandable portion 135a may have a folded or pleated structure during delivery that expands or unfolds upon deployment to a larger-diameter cross-section. FIGS. 4C and 4D are transverse cross-sectional views of the first sheath 135 that illustrate how the expandable portion 135a of the sheath 135 may radially expand upon deployment from the low-profile configuration used for delivery to a radially expanded state. It is also contemplated that the expandable portion 135a may be formed of a highly elastic material that can stretch from a smaller diameter to a larger diameter.

Generally, the expandable portion 135a is disposed proximally adjacent to the grasping component 115 when in the low-profile configuration inside the second sheath 150. However, it is contemplated that the expandable portion 135a may alternatively overlie all or a portion of the grasping component 115 in the low-profile configuration.

Preferably, the expandable portion 135a of the first sheath 135 includes an arrangement of barbs 140 on an inner wall 135i thereof. When the expandable portion 135a is deployed, as shown in the cross-sectional view of FIG. 4D, the barbs 140 are configured to anchor into structural elements of the medical device to be retrieved. Accordingly, the medical device may be captured so that when the first sheath 135 is retracted, the medical device moves along with it. All or a portion of the medical device may be covered by the expandable portion 135a. Retraction and advancement of the first sheath 135 are controlled by a handle 165 at the proximal end 100b of the system 100.

The barbs 140 extending from the inner wall 135i of the first sheath 135 may be attached to or integrally formed with a frame 145 that forms part of the first sheath 135. The frame 145 is preferably made of a resilient or superelastic material. The frame 145 may be partially or fully embedded in the inner wall 135i of the first sheath 135, which is preferably formed of a biocompatible polymer. Suitable materials for the first sheath 135 and frame 145 are discussed in greater detail below.

FIG. 5 shows a tubular second sheath 150 having a distal end 150a that overlies the first sheath 135 and the grasping component 115 during delivery and retrieval of the system 100. The second sheath has a proximal end 150b connected to a handle 155 for manipulation by a clinician.

Referring again to FIG. 1A, the barbs 140 of the first sheath 135 extend away from the inner wall 135i and are preferably angled toward the proximal end 100b of the system 100. In a lengthwise direction, the arrangement of barbs 140, where the arrangement includes the barbs 140 and the spaces between adjacent barbs 140, may extend over substantially the entire length of the expandable portion 135a of the first sheath 135. Typically, the length of the expandable portion is in the range of from about 10 mm to about 300 mm, which is sufficient to substantially cover the medical device to be retrieved. For example, the length may lie in the range of from about 10 mm to about 200 mm. Shorter or longer lengths are also possible depending on needs. The arrangement of barbs 140 also extends over at least a portion of the circumference of the expandable portion 135a of the first sheath 135. Preferably, as shown in FIGS. 4C and 4D, the arrangement of barbs 140 extends symmetrically about the entire circumference of the inner wall 135i of the expandable portion 135a.

The arrangement of barbs 140 may be a regular arrangement. As shown in FIG. 1A, for example, the barbs 140 may be regularly arranged about the circumference of the inner wall 135i, and they may also be regularly arranged along the length. The desired spacing between adjacent barbs 140 is generally determined by the strut or mesh pattern of the stent or other medical device to be retrieved using the retrieval system 100. Preferably, each barb 140 has a length that is substantially equal to or greater than a wall thickness of the structural elements of the medical device so as to ensure secure anchoring of the device. For example, the length of each barb 140 may be in the range of from about 0.05 mm to about 1 mm. The length may also be in the range of from about 0.1 mm to about 0.4 mm.

Like the arrangement of barbs 140, the metallic frame 145 preferably extends over substantially the entire length and circumference of the expandable portion 135a of the first sheath 135. The metallic frame 145 is advantageously formed of a shape memory material that can automatically deploy from a collapsed configuration, such as that shown in FIG. 4C, to an expanded deployed configuration, such as that shown in FIG. 4D, in response to a change in temperature (shape memory effect) or the removal of an applied stress (superelastic effect). Similarly, the barbs 140 may also be formed of a shape memory material and may have different low-profile and deployed configurations, such as a retracted state and an extended state. It is also contemplated that the deployable arms 120 of the grasping component 115 may be advantageously made of a shape memory material so as to automatically change from a low-profile to a deployed configuration in response to a change in temperature or applied stress.

The shape memory material of the deployable arms, frame and/or barbs may be a shape memory polymer or a shape memory alloy, such as a nickel-titanium alloy. As is well known in the art, equiatomic or near-equiatomic nickel-titanium alloys, such as Nitinol, undergo a reversible phase transformation between a martensitic phase and an austenitic phase that allows a previous configuration to be "remembered" and recovered. For example, compressive strain imparted to a martensitic component to achieve a low-profile delivery configuration may be substantially recovered during a reverse phase transformation to austenite, such that the component reverts to a "remembered" (e.g., expanded) configuration at a treatment site in a vessel. Typically, recoverable strains of about 8-10% may be obtained from superelastic nickel-titanium alloys.

As generally understood by those skilled in the art, martensite start temperature ($M_s$) refers to the temperature at which a phase transformation to martensite begins upon cooling for a nickel-titanium shape memory alloy, and martensite finish temperature ($M_f$) refers to the temperature at which the phase transformation to martensite concludes. Austenite start temperature ($A_s$) refers to the temperature at which a phase transformation to austenite begins upon heating for a nickel-titanium shape memory alloy, and austenite finish temperature ($A_f$) refers to the temperature at which the phase transformation to austenite concludes.

For values of $A_f$ at or below body temperature, the deployment of a nickel-titanium alloy component of the system 100 (e.g., the barbs 140, frame 145, and/or deployable arms 120) may occur (1) by the shape memory effect as the component warms up by exposure to body temperature, or (2) superelastically upon removal of a restraining force (e.g., retraction of the second sheath). Slightly nickel-rich Nitinol alloys including, for example, about 51 at. % Ni and about 49 at. % Ti are known to be useful for medical devices which are superelastic at body temperature. In particular, alloys including 50.6-50.8 at. % Ni and 49.2-49.4 at. % Ti are considered to be medical grade Nitinol alloys and are suitable for the present frame 145 and/or barbs 140. The nickel-titanium alloy may further include one or more additional alloying elements that substitute for one or both of the nickel and titanium atoms. Suitable nickel-titanium alloys may be obtained from any of a number of commercial sources.

The alloys may be cold worked into desired shapes (e.g., wires or tubes) by, for example, drawing, rolling, or another forming method. The cold working typically involves several forming passes in combination with interpass annealing treatments at temperatures in the range of from about 600° C. to about 800° C. The interpass annealing treatments soften the material between cold work passes, which typically impart 30-40% deformation to the material. Machining operations, such as, for example, drilling, cylindrical centerless grinding, or laser cutting may also be employed to fabricate the desired component (e.g., the deployable arms, frame and/or barbs).

A heat treatment may be employed to impart a "memory" of a desired high temperature shape and to optimize the shape memory/superelastic and mechanical properties of the component. The number, duration and the temperature of the heat treatments can affect the transformation temperatures. Typically, heat treatment temperatures of 400° C. to 550° C. are appropriate to set the final shape and to optimize the properties.

The first and second sheaths 135, 150 are generally made of one or more biocompatible polymers, such as, for example, a polyamide (e.g., nylon) or PTFE, and may further include a lubricious coating on an inner and/or outer surface thereof. The first and second sheaths 135, 150 may be fabricated by extrusion methods known in the art. To form the expanded portion 135a of the first sheath 135, one end of an extruded tube may undergo an elevated temperature forming process using a tapered mandrel to create a radially-flared wall. A metal frame and barbs may be embedded within the wall by, for example, disposing the metal frame and barbs adjacent to the wall, applying a polymer layer over the frame and barbs, and applying heat and pressure to bond the polymer layer to the flared wall.

The cannula 110 may be made of a biocompatible metal or alloy, such as stainless steel, or a biocompatible polymer such as, for example, a polyamide (e.g., nylon), fluorocarbon (e.g., polytetrafluoroethylene (PTFE)), polyether block amide (PEBA), polyolefin, or polyimide. Conventional manufacturing methods known in the art for fabricating tubing, such as extrusion and drilling, may be employed to form the cannula. The push rod 125 and tip 130 also may be fabricated using known tube forming methods, preferably from a biocompatible polymer such as a polyurethane or nylon. The tip 130 may be made from the same tubing as the push rod 125 by cutting a tube of the appropriate size (e.g., about 3 cm in length) from the tubing, and warm forming the tube with a mold to create a tapered end.

The retrieval system 100 may be sized to fit within an introducer of from 5 Fr to 12 Fr in size. Preferably, the system 100 is sized to fit within an introducer of from 8 Fr to 10 Fr in size. The system may have a length of from about 80 cm to about 135 cm, typically.

The grasping component 115 may be formed of a polymer, a metal, or both. For example, the grasping component 115 may be fabricated from a biocompatible polymer tube that is cut to create two or more longitudinally extending arms and then formed at elevated temperatures with a tapered mandrel or the like to obtain a radially expanded configuration of the arms. Due to the elastic nature of the polymer, the arms 120 may be constrained in a low profile state by a tubular sheath for delivery and may expand automatically upon removal of the sheath. Alternatively, the arms 120 of the grasping component 115 may be laser cut from a metal tube and then heat-set or otherwise formed to deploy automatically when advanced out of an overlying sheath. The metal tube may be formed of stainless steel, Nitinol, cobalt-chrome, or another suitable biocompatible alloy. According to one embodiment, the arms 120 may be formed of separate segments of stainless steel, for example, that are partially embedded in the distal tip 130 in a cantilever configuration.

Radiopaque markers may be attached to various components of the deployment system, including, for example, the first sheath 135, the second sheath 150, the grasping component 115, and the deployable arms 120. These markers may be made of a radiopaque material, that is, a material that strongly absorbs x-ray radiation and is thus readily visible using an x-ray imaging device, such as a fluoroscope. Preferably, the radiopaque material is also biocompatible. The radiopaque material may include, for example, gold, iridium, niobium, palladium, platinum, silver, tantalum, tungsten, or an alloy thereof, such as platinum-iridium.

Figure 6:
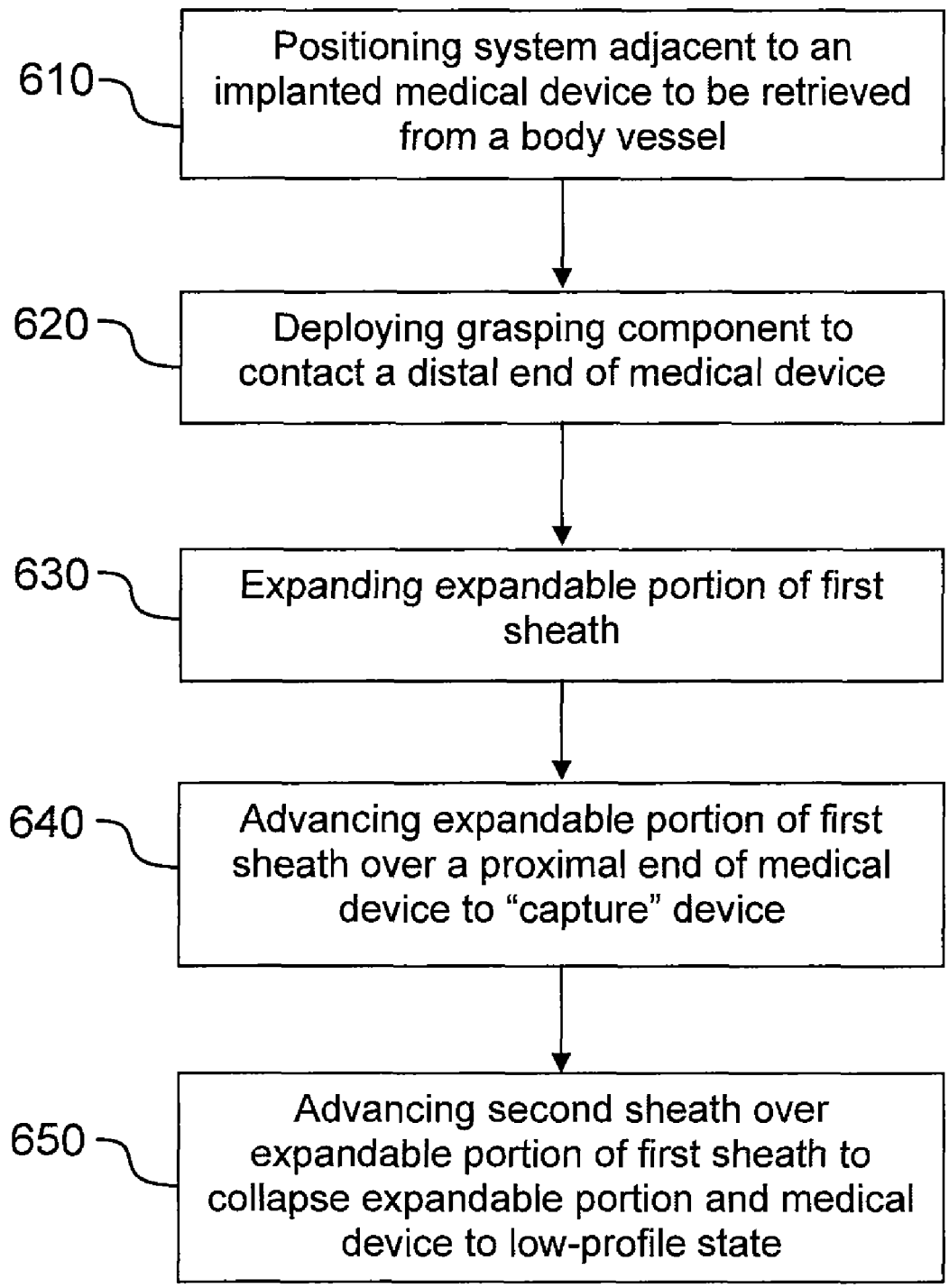
FIG. 6 is a flow chart describing, according to one aspect, a method of retrieving an implantable medical device from a body vessel.

Referring to the flow chart of FIG. 6, a method of using the retrieval system includes, according to one aspect, positioning 610 the retrieval system adjacent to an implanted medical device to be retrieved from a body vessel, where the retrieval system includes a grasping component, a first sheath having an expandable portion disposed adjacent to the grasping component, and a second sheath overlying the first sheath and the grasping component.

The retrieval system may be introduced into the body using standard techniques for obtaining safe access to body vessels, such as the well-known Seldinger technique. For example, a hollow needle may be used to penetrate the vessel of interest, and a wire guide may be threaded through the needle into the vessel. The needle can then be removed and replaced with an introduction catheter, and the retrieval system may then be passed over the wire guide and delivered through the introduction catheter to gain access to the vessel. Alternatively, the presence of a tapered tip 130 on the retrieval system 100, as shown for example in FIG. 2, may allow the retrieval system 100 to be introduced into the body vessel without an introduction catheter.

Once in the desired position within the vessel, the grasping component is deployed 620 to contact a distal end of the medical device. The expandable portion of the first sheath is expanded 630 and advanced 640 over a proximal portion of the medical device. Preferably, the expandable portion of the first sheath includes an arrangement of barbs on an inner wall thereof to facilitate "capturing" the medical device. The second sheath is then advanced 650 over the expandable portion of the first sheath to collapse the expandable portion and the captured medical device to a low-profile configuration. The grasping component is also collapsed by, for example, advancing the second sheath or activating an umbrella mechanism, and the system, including the medical device, may be retracted and removed from the body vessel.

FIGS. 7A-7G show schematically the steps in an exemplary process of retrieving a balloon-expandable stent that failed to deploy fully at a treatment site in a vessel. The figures are also illustrative of the retrieval of a self-expanding stent that was improperly sized relative to the vessel diameter and is therefore not securely fixed in place in the vessel.

Figure 7A:
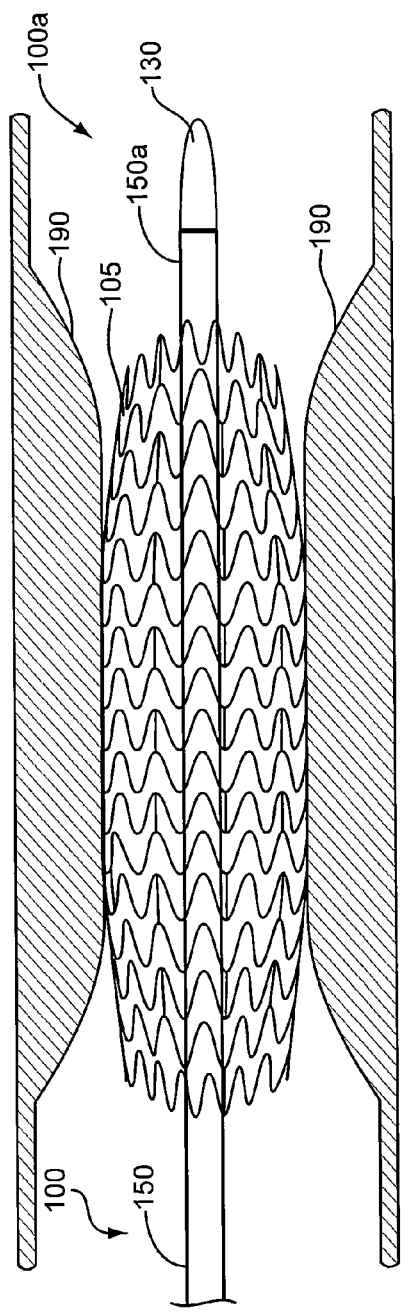

Referring to FIG. 7A, the system 100 is inserted into a body vessel 190 and positioned at the site of the partially deployed or undersized stent 105. The second sheath 150 is retracted or the push rod 125 is moved forward by a clinician to advance the grasping component 115 out of the second sheath 150, thereby allowing arms 120 of the grasping component 115 to be deployed. When deployed, proximal ends 120b of the deployable arms 120 extend away from a longitudinal axis of the system 100. In this example, the deployable arms 120 self-extend into their deployed configuration when outside the second sheath 150. The positioning of the grasping component 115 with respect to the stent 105 can be adjusted by moving the push rod 125 in a distal and/or proximal direction, and the deployable arms 120 can thus be brought into contact with the distal end of the stent 105.

Figure 7B:
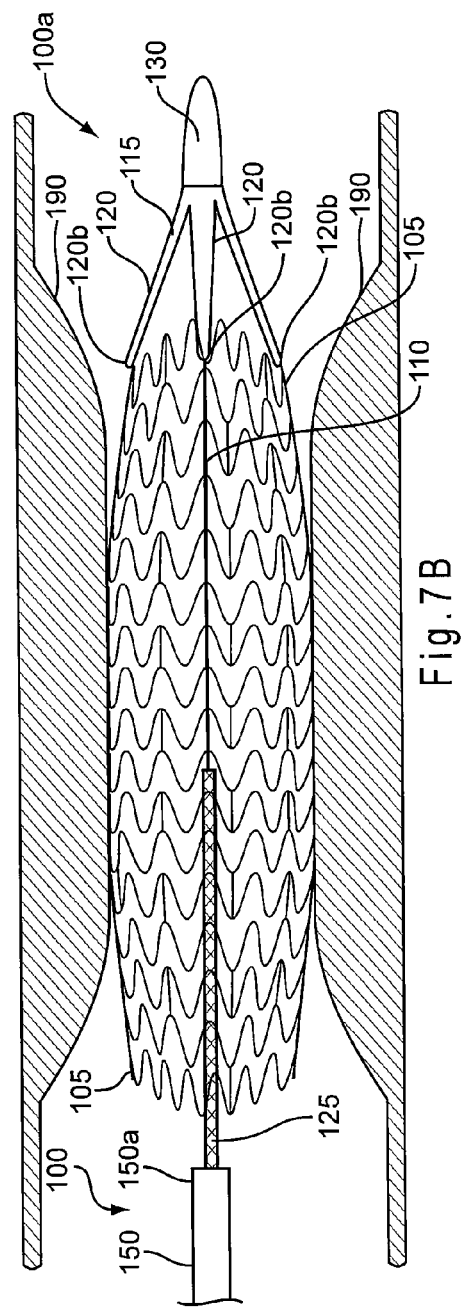

Referring to FIG. 7B, after deployment of the grasping component 115, the first and second sheaths 135, 150 are retracted to a position proximal to the proximal end of the stent 105.

The second sheath 150 is then further retracted, as shown in FIG. 7C, to allow a distal expandable portion 135a of the first sheath 135 to expand. The expandable portion 135a preferably includes on an inner wall 135i a self-expanding metal frame 145 and barbs 140 (as discussed above and which are visible in FIG. 1A).

FIG. 7D shows the expandable portion 135a of the first sheath 135 being pushed over a proximal portion of the stent so as to "capture" the stent 105. As the first sheath 135 is advanced, the barbs 140 of the expandable portion 135a ratchet over struts of the stent 105 and ultimately become anchored between adjacent struts. The expandable portion 135a may be advanced over all or a portion of the stent 105. The grasping component 115 helps to maintain the position of the stent 105 as the first sheath 135 is advanced.

Referring to FIGS. 7E and 7F, the second sheath 150 is then advanced over the first sheath 135 to collapse the expandable portion 135a of the first sheath 135 and the captured stent 105 to a low-profile configuration. The second sheath 150 is further advanced to cause the deployable arms 120 to collapse. The first sheath 135 may also or alternatively be advanced to collapse the deployable arms 120. Ultimately, the second sheath 150 overlies the expandable portion 135a of the first sheath 135, the captured stent 105, and the deployable arms 120.

Figure 7G:
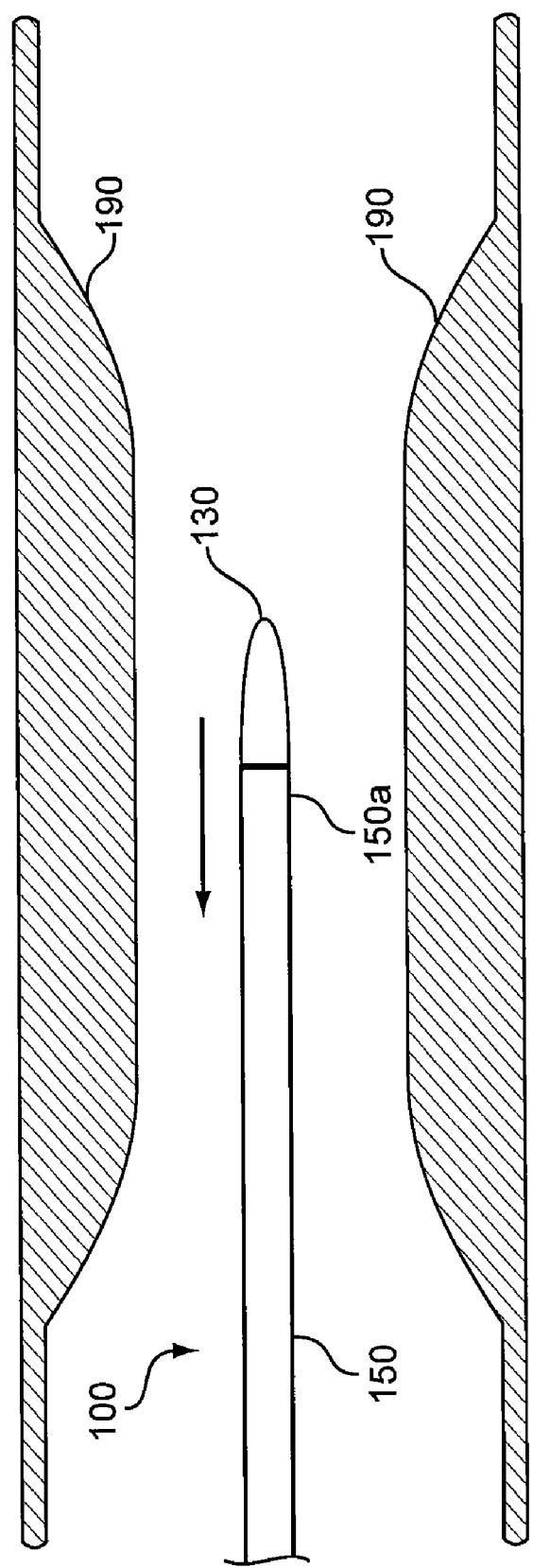

As depicted in FIG. 7G, once in the collapsed, low-profile configuration, the retrieval system 100, including the captured medical device (stent 105), may be removed from the body without causing damage to the vessel.

FIGS. 8A-8G show schematically the steps in an exemplary process of retrieving a self-expanding stent that has been positioned at an undesirable site in a vessel 190. In contrast with the partially deployed or undersized stent 105 shown in FIGS. 7A-7G, the deployed stent 205 of FIGS.

8A-8G is substantially fully in contact with the vessel walls but placed at an incorrect location. In this example, it is particularly important that the proximal ends 220b of the deployable arms 220 and the expandable portion 235a of the first sheath 235 expand to a diameter sufficient to respectfully contact and capture the expanded stent 205. Also, in contrast to the retrieval process of FIGS. 7A-7G, an umbrella mechanism is employed in FIGS. 8A-8G to extend and collapse the arms 220 of the grasping component 215.

Referring to FIG. 8A, the system 200 is inserted into the body vessel 190 and positioned at the site of the improperly placed stent 205. The second sheath 250 is retracted or the push rod 225 is pushed forward by a clinician to advance the grasping component 215 out of the second sheath 250, thereby allowing arms 220 of the grasping component 215 to be deployed. When deployed, the proximal ends 220b of the deployable arms 220 extend away from a longitudinal axis of the system 200. In this example, the grasping component 215 is manually deployed by way of the umbrella mechanism 175 and controller 170 shown in FIGS. 3C-3E and discussed previously. The positioning of the grasping component 215 with respect to the stent 205 can be adjusted by moving the push rod 225 in a distal and/or proximal direction, and the deployable arms 220 can thus be brought into contact with the distal end of the stent 205.

Referring to FIG. 8B, after deployment of the grasping component 215, the first and second sheaths 235, 250 are retracted to a position proximal to the proximal end of the stent 205.

The second sheath 250 is then further retracted, as shown in FIG. 8C, to allow a distal expandable portion 235a of the first sheath 235 to expand. The expandable portion 235a preferably includes on an inner wall 235i a self-expanding metal frame 145 and barbs 140 (as discussed above and which are visible in FIG. 1A).

FIG. 8D shows the expandable portion 235a of the first sheath 235 being pushed over a proximal portion of the stent so as to "capture" the stent 205. As the first sheath 235 is advanced, the barbs 140 of the expandable portion 235a ratchet over struts of the stent 205 and ultimately become anchored between adjacent struts. The expandable portion 235a may be advanced over all or a portion of the stent 205. The grasping component 215 helps to maintain the position of the stent 205 as the first sheath 235 is advanced.

Figure 8E:
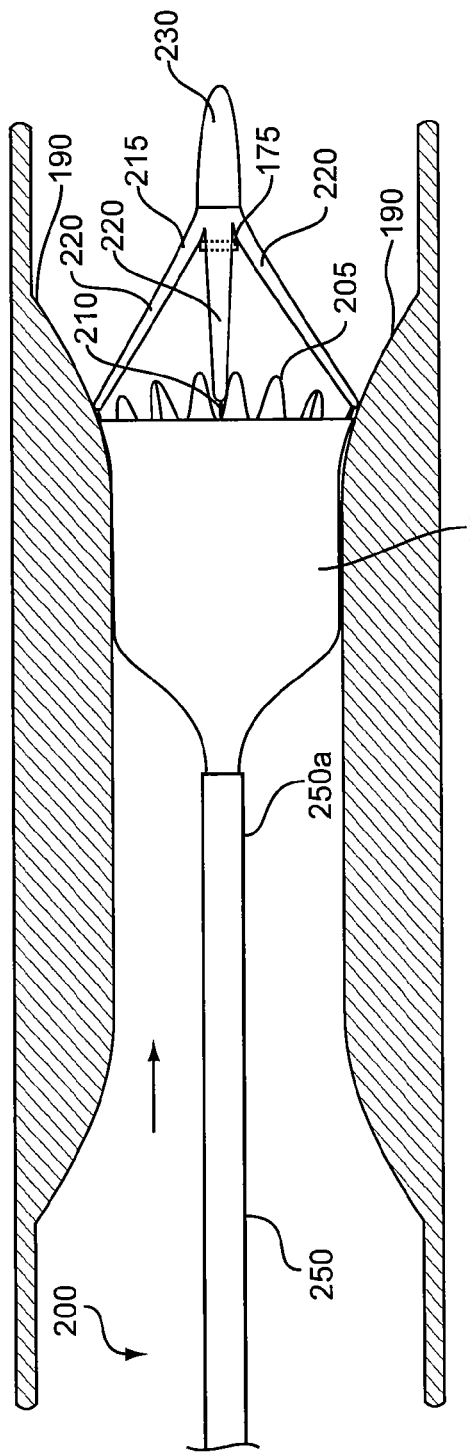
Figure 8F:
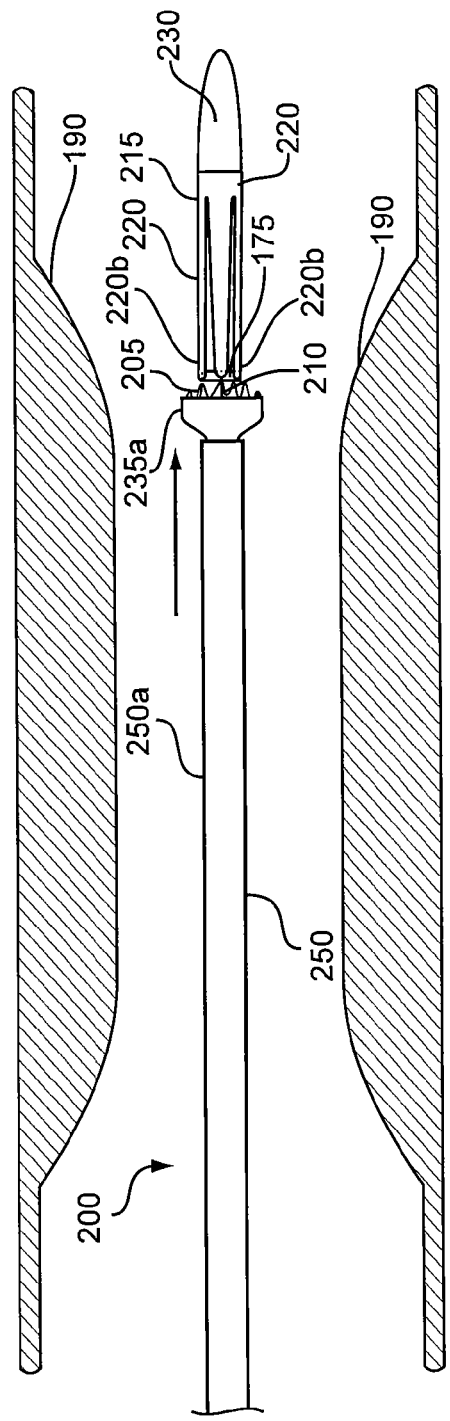

Referring to FIGS. 8E and 8F, the second sheath 250 is then advanced over the first sheath 235 to collapse the expandable portion 235a of the first sheath 235 and the captured stent 205 to a low-profile configuration. The push rod 225 may be advanced forward slightly to disengage the grasping component 215 from the stent 205, and the proximal portion 170b of the controller 170 (visible in FIGS. 3C through 3E) may be translated away from the distal portion 170a to retract the umbrella mechanism 175 and cause the deployable arms 220 to collapse. The second sheath 250 is then further advanced over the collapsed arms 220 of the grasping component 215.

Figure 8G:
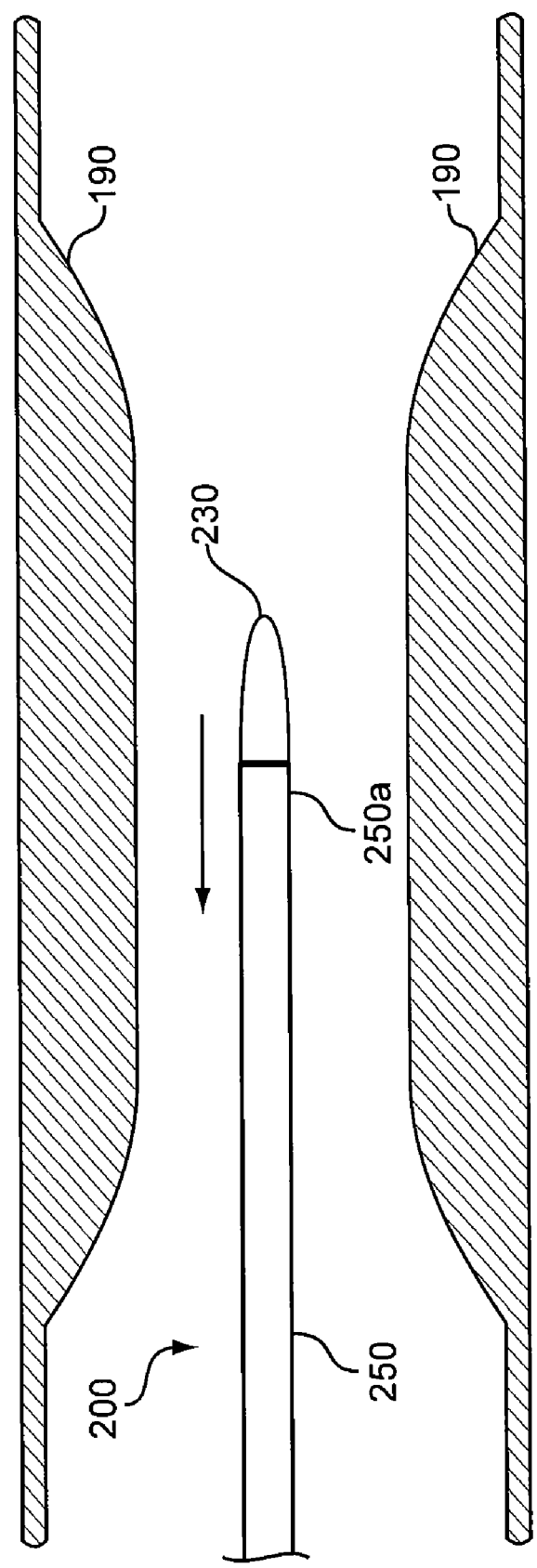

As depicted in FIG. 8G, once in the collapsed, low-profile configuration, the retrieval system 200, including the captured medical device (stent 205), may be removed from the body without causing damage to the vessel.

An intraluminal system that can safely and effectively retrieve an implanted medical device from a body vessel without surgery has been described. A method of retrieving an implanted medical device from a body vessel has also been described. The intraluminal system and method are designed to allow the implanted device to be collapsed to a low-profile configuration and retrieved from the vessel without causing damage to the surrounding tissue.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

What is claimed is:

1. A method of retrieving a medical device from a body vessel, the method comprising:
    positioning a retrieval system adjacent to a medical device to be removed from a body vessel, the retrieval system including a grasping component with a plurality of arms coupled to a distal tip, a first sheath having a radially expandable portion disposed adjacent to the grasping component, and a second sheath overlying the first sheath and the grasping component;
    deploying the grasping component to contact a distal end portion of the medical device by opening the plurality of arms in a proximal facing direction of the retrieval system;
    expanding the expandable portion of the first sheath;
    advancing the expandable portion over a proximal portion of the medical device;
    advancing a second sheath over the expandable portion of the first sheath to collapse the expandable portion and the medical device;
    collapsing the plurality of arms of the grasping component; and
    removing the system including the medical device from the body vessel.

2. The method of claim 1, wherein deploying the grasping component comprises moving the second sheath and the grasping component relative to each other.

3. The method of claim 2, wherein deploying the grasping component comprises retracting the second sheath.

4. The method of claim 2, wherein deploying the grasping component further comprises advancing an annular fixture of an umbrella mechanism in communication with the plurality of arms of the grasping component, and wherein collapsing the plurality of arms of the grasping component comprises retracting the annular fixture of the umbrella mechanism.

5. The method of claim 1, wherein expanding the expandable portion of the first sheath comprises moving the second sheath and the first sheath relative to each other.

6. The method of claim 1, further comprising retracting the first sheath to a position proximal to the proximal portion of the medical device prior to expanding the expandable portion.

7. The method of claim 1, wherein collapsing the grasping component comprises advancing at least one of the second sheath and the first sheath over the grasping component.

8. The method of claim 1, wherein deploying the grasping component comprises advancing the grasping component out of the second sheath, and wherein expanding the expandable portion comprises retracting the second sheath, and further comprising retracting the first sheath to a position proximal to the proximal portion of the medical device prior to expanding the expandable portion, and wherein collapsing the grasping component comprises advancing the second sheath thereover.

9. The method of claim 1, wherein advancing the expandable portion over the proximal portion of the medical device comprises ratcheting a plurality of barbs extending from an inner wall of the expandable portion over structural elements of the medical device thereby anchoring the medical device to the first sheath.

* * * * *

UNITED STATES PATENT AND TRADEMARK OFFICE
CERTIFICATE OF CORRECTION

PATENT NO. : 8,034,095 B2  Page 1 of 1
APPLICATION NO. : 12/201556
DATED : October 11, 2011
INVENTOR(S) : James R. Randolph et al.

It is certified that error appears in the above-identified patent and that said Letters Patent is hereby corrected as shown below:

In the Claims

In column 10, claim 1, line 21, before "of the medical device by" delete "portion".

Signed and Sealed this
Tenth Day of July, 2012

David J. Kappos
*Director of the United States Patent and Trademark Office*